(12) United States Patent
Blaskovich et al.

(10) Patent No.: US 8,360,765 B2
(45) Date of Patent: Jan. 29, 2013

(54) SYSTEMS AND METHOD FOR FORMING A COAXIAL IMPLANT

(75) Inventors: Phillip Blaskovich, Salem, MA (US);
Derek Rissman, Waltham, MA (US);
Steven Bennett, Cheshire, CT (US);
Rachit Ohri, Framingham, MA (US);
Arthur Driscoll, Reading, MA (US)

(73) Assignee: Covidien LP, Mansfield, MA (US)

( * ) Notice: Subject to any disclaimer, the term of this patent is extended or adjusted under 35 U.S.C. 154(b) by 41 days.

(21) Appl. No.: 12/986,201

(22) Filed: Jan. 7, 2011

(65) Prior Publication Data
US 2012/0175810 A1 Jul. 12, 2012

(51) Int. Cl.
*B29C 45/14* (2006.01)
*B29C 45/13* (2006.01)

(52) U.S. Cl. ............ 425/120; 264/313; 264/328.7; 264/328.8; 264/267; 264/255; 425/130

(58) Field of Classification Search .................. None
See application file for complete search history.

(56) References Cited

U.S. PATENT DOCUMENTS

| | | | |
|---|---|---|---|
| 786,518 A * | 4/1905 | Roberts | 313/354 |
| 1,646,356 A * | 10/1927 | Johnson | 264/267 |
| 3,100,677 A * | 8/1963 | Frank et al. | 264/71 |
| 4,186,162 A * | 1/1980 | Daley | 264/46.5 |
| 4,519,973 A * | 5/1985 | Cahalan et al. | 264/267 |
| 4,691,432 A * | 9/1987 | Haren et al. | 29/527.2 |
| 4,874,368 A * | 10/1989 | Miller et al. | 604/82 |
| 5,266,325 A * | 11/1993 | Kuzma et al. | 424/422 |
| 5,389,312 A * | 2/1995 | Lebby et al. | 264/1.24 |
| 5,626,611 A | 5/1997 | Liu et al. | |
| 5,697,903 A * | 12/1997 | Fischer | 604/82 |
| 5,834,001 A | 11/1998 | Dionne et al. | |
| 5,840,227 A * | 11/1998 | Bourdoncle et al. | 264/112 |
| 5,876,288 A * | 3/1999 | Jaskowiak | 464/181 |
| 6,093,200 A | 7/2000 | Liu et al. | |
| 6,231,798 B1 * | 5/2001 | Matsumoto et al. | 264/255 |
| 6,315,788 B1 | 11/2001 | Roby | |
| 6,602,261 B2 | 8/2003 | Greene, Jr. et al. | |
| 6,605,294 B2 | 8/2003 | Sawhney | |
| 6,632,457 B1 | 10/2003 | Sawhney | |
| 6,841,244 B2 | 1/2005 | Foss et al. | |
| 6,946,196 B2 | 9/2005 | Foss | |
| 7,014,645 B2 | 3/2006 | Greene, Jr. et al. | |
| 7,255,874 B1 | 8/2007 | Bobo et al. | |
| 7,288,084 B2 | 10/2007 | Li | |
| 7,329,414 B2 | 2/2008 | Fisher et al. | |
| 7,491,214 B2 | 2/2009 | Greene, Jr. et al. | |
| 7,737,060 B2 | 6/2010 | Strickler et al. | |
| 2003/0187476 A1 | 10/2003 | Im et al. | |
| 2003/0203003 A1 | 10/2003 | Nelson et al. | |
| 2004/0009205 A1 | 1/2004 | Sawhney | |
| 2004/0030262 A1 | 2/2004 | Fisher et al. | |
| 2004/0076579 A1 | 4/2004 | Coniglione et al. | |
| 2004/0209059 A1 | 10/2004 | Foss | |
| 2004/0214495 A1 | 10/2004 | Foss et al. | |
| 2004/0215169 A1 | 10/2004 | Li | |
| 2005/0171572 A1 | 8/2005 | Martinez | |
| 2006/0067882 A1 | 3/2006 | Russell et al. | |
| 2006/0240071 A1 | 10/2006 | Lerner et al. | |
| 2007/0141106 A1 | 6/2007 | Bonutti et al. | |
| 2007/0191781 A1 | 8/2007 | Richards et al. | |
| 2007/0213660 A1 | 9/2007 | Richards et al. | |
| 2008/0091120 A1 | 4/2008 | Fisher | |
| 2008/0097521 A1 | 4/2008 | Khosravi et al. | |

(Continued)

*Primary Examiner* — Edmund H. Lee

(57) ABSTRACT

The present disclosure provides implants suitable for drug delivery. In embodiments, the present disclosure provides layered biodegradable drug delivery implants and systems and methods for making these implants.

17 Claims, 9 Drawing Sheets

U.S. PATENT DOCUMENTS

| | | |
|---|---|---|
| 2008/0161848 A1 | 7/2008 | Fisher |
| 2009/0011038 A1 | 1/2009 | Seiler et al. |
| 2009/0048558 A1 | 2/2009 | Del Vecchio |
| 2009/0155326 A1 | 6/2009 | Mack et al. |
| 2009/0214373 A1 | 8/2009 | Stinson et al. |
| 2010/0168007 A1 | 7/2010 | Cruise et al. |

* cited by examiner

    
FIG. 5A  FIG. 5B  FIG. 5C  FIG. 5D  FIG. 5E
    
FIG. 5F  FIG. 5G  FIG. 5H  FIG. 5I  FIG. 5J
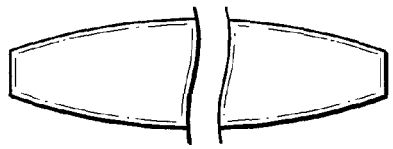 
FIG. 6A  FIG. 6B
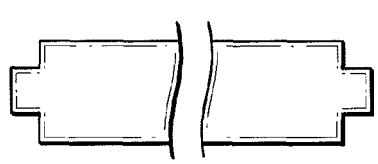 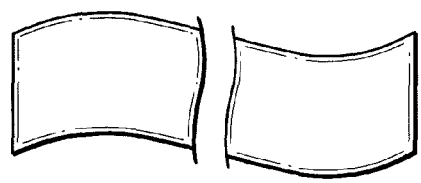
FIG. 6C  FIG. 6D the entire disclosure of which is incorporated by

SYSTEMS AND METHOD FOR FORMING A COAXIAL IMPLANT

BACKGROUND

1. Technical Field

The present disclosure generally relates to drug delivery implants. More particularly, the present disclosure relates to layered biodegradable drug delivery implants and systems and methods for making the implants.

2. Background of Related Art

Many therapeutic agents (TAs) and active pharmaceutical ingredients (APIs) are known. As discussed in U.S. Pat. No. 6,632,457 the entire disclosure of which is incorporated by reference herein, hydrogels may be used to form delivery implants for the controlled release of TAs and APIs. These drug delivery implants are typically preformed, and thus, provided to a clinician with one or more predetermined TAs and/or APIs, in predetermined concentrations, configured to be dispensed at predetermined rates.

Customizing an implant for a given patient and/or procedure using current implant forming methods may thus be cost and/or time prohibitive. Further, many TAs and/or APIs begin to denature upon formation, thus limiting the shelf-life of an implant and/or the agents and/or ingredients that may be used in the implant.

Improved systems and methods for making drug delivery implants that may be preformed, i.e., in an operating room during a surgical procedure, remain desirable.

SUMMARY

The present disclosure provides systems for forming implants, methods for forming such implants, as well as implants formed thereby. In embodiments, a system of the present disclosure includes a system for forming a coaxial implant including a first assembly for dispensing a first material; a second assembly for dispensing a second material; a sleeve defining first and second ends and defining a cavity therebetween for forming an implant, wherein the first and second ends are configured for operable engagement with each of the first and second assemblies; and a centering post configured for operable engagement with the sleeve.

A method of the present disclosure includes, in embodiments, a method of forming a coaxial implant including providing a system including first and second dispensing assemblies, an implant forming sleeve having two ends, and a centering post; selectively securing the first dispensing assembly and the centering post with a first end of the implant forming sleeve; activating the first dispensing assembly to deposit a first material within the sleeve and about the centering post to form a first layer of the implant; separating the centering post from the sleeve; selectively securing the second dispensing assembly with a second end of the implant forming sleeve; activating the second dispensing assembly to deposit a second material within the sleeve to form a core of the implant; and separating the first and second dispensing assemblies from the sleeve.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 5A-5J are end views of sleeves according to alternative embodiments of the present disclosure;

FIGS. 6A-6D are side views of sleeves according to alternative embodiments of the present disclosure;

DETAILED DESCRIPTION

Figure 1:
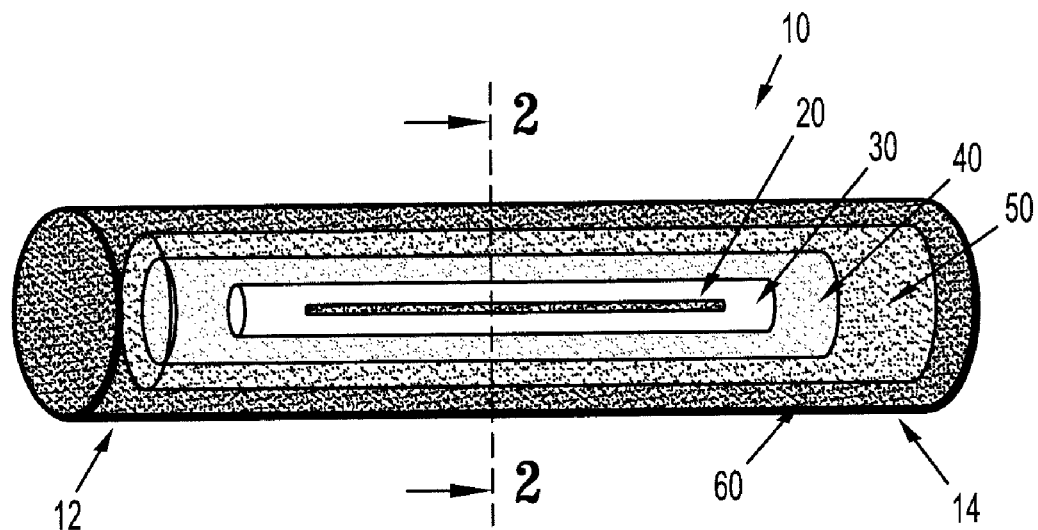
FIG. 1 is side view of a coaxial implant according to an embodiment of the present disclosure.
Figure 2:
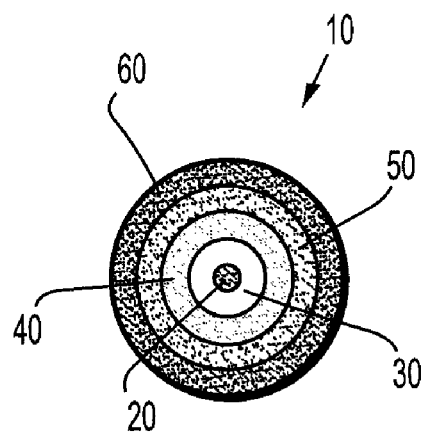
FIG. 2 is a cross-sectional view of the implant of FIG. 1 taken along line 2-2 of FIG. 1.

Referring initially to FIGS. 1 and 2, a delivery implant according to an embodiment of the present is shown generally as implant 10. Implant 10 includes a core 20, a first layer or coating 30, a second layer or coating 40, a third layer or coating 50, and a fourth layer or overcoat 60. First layer 30 is formed about core 20. Second layer 40 is formed about first layer 30. Third layer 50 is formed about second layer 40. Overcoat 60 is formed about third layer 50. As shown, each of first layer 30, second layer 40, third layer 50 and overcoat 60 fully encase respective core 20, first layer 30, second layer 40 and third layer 50. In this manner, each of overcoat 60, third layer 50, second layer 40 and first layer 30 must degrade before each subsequent inner layer is exposed.

In embodiments, any or all of core 20, first layer 30, second layer 40, and third layer 50 may extend the entire length of one or more of the subsequent outer layers, thereby exposing one or both of the ends thereof. As will be discussed in further detail below, the exposed ends may allow for coaxial degradation of the layer.

Although shown including a core, three (3) layers and an overcoat, it is envisioned that implant 10 may include a core and more or less than 3 layers. In embodiments, implant 10 does not include an overcoat 60.

Each of first, second and third layers 30, 40, 50, and overcoat 60, may be of equal or different thicknesses. In this manner, each of first, second and third layers 30, 40, 50 and overcoat 60 may degrade at the same or different rates. As shown, implant 10 and core 20 include a substantially cylindrical body having a circular cross-sectional shape. It is envisioned that either or both of implant 10 and core 20 may include alternative cross-sectional shapes, e.g., square, pentagonal, octagonal. It is further envisioned that core 20 may include one or more radial projections or may be otherwise configured to modify the degradation rate of implant 10 in general, and core 20, specifically.

With reference still to FIGS. 1 and 2, each of core 20, first layer 30, second layer 40, third layer 50 and overcoat 60 may include one or more polymers and/or one or more hydrogels. The hydrogels may be based upon natural materials, synthetic materials, combinations thereof, and the like. In embodiments, suitable hydrogels include those using synthetic precursors within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other suitable hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

In addition to the above hydrogels, an implant formed in accordance with the present disclosure may include other biocompatible polymers. Suitable biocompatible polymers may also be natural or synthetic materials. In embodiments, the biocompatible polymers may be biodegradable. Biodegradable materials include natural collagenous materials, cat gut, celluloses, including carboxymethyl cellulose, and/or hyaluronic acid, as well as synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, copolymers thereof, combinations thereof, and the like. For example, in embodiments, In embodiments, overcoat 60 may be formed of an absorbable material such as cellulose.

The type and/or composition of the polymer and/or hydrogel used in each of core 20, layers 30, 40, 50, and overcoat 60, may be the same or different. The hydrogels used to form implant 10 may be hydrated or dehydrated. Each of core 20, layers 30, 40, 50, and overcoat 60, may further include one or more therapeutic agents (TAs) and/or one or more active pharmaceutical ingredients (APIs). The one or more TAs and/or one or more APIs used in each of core 20, first, second and third layers 30, 40, 50, and overcoat 60, and the concentration of each, may be the same or different. A polymeric coating (not shown) may be provided between one or more of core 20, first layer 30, second layer 40, third layer 50 and overcoat 60. For example, in embodiments, polylactide, or a polylactide-co-glycolide coating may be provided between one or more of core 20, first layer 30, second layer 40, third layer 50 and overcoat 60. It is envisioned that the polymeric coating between layers may impart hydrophobocity to reduce the swell time of each layer, 30, 40, 50, as well as overcoat 60. The polymeric coating between layers may also provide support to implant 10.

As discussed above, one or more of core 20, first, second and third layers 30, 40, 50, and overcoat 60, of implant 10 may include exposed first and/or second ends. Either or both of ends 12, 14 of implant 10 may be dipped into a polymeric material to seal either or both of the first and second ends of core 20, first, second and third layers 30, 40, 50, and overcoat 60. Sealing ends 12, 14 of implant 10 ensures that the release of the one or more TAs and/or one or more APIs contained within each of core 20, first, second and third layers 30, 40, 50, and overcoat 60, may be radial or tangential.

Figure 3:
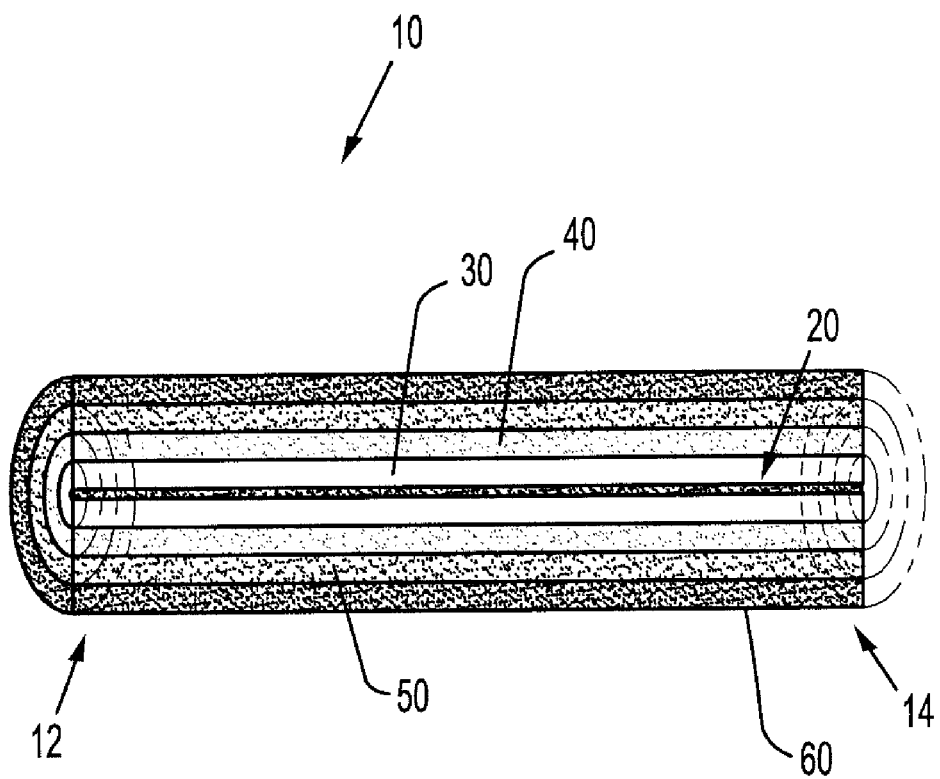
FIG. 3 is a side view of an implant according to an alternative embodiment of the present disclosure.

Turning briefly to FIG. 3, in an alternative embodiment, each of core 20, first, second and third layers 30, 40, 50, and overcoat 60, extends the length of implant 10. As shown, ends 12, 14 of implant 10 are left open, thereby exposing both ends of core 20, first, second and third layers 30, 40, 50, and overcoat 60. In this manner, the one or more TAs and/or APIs in each of core 20, first, second and third layers 30, 40, 50, and overcoat 60 may be released longitudinally from implant 10. In embodiments, it is envisioned that only one of the ends 12, 14 may be sealed (not shown) to allow for slower longitudinal radial release of the one or more TAs and/or APIs from implant 10.

Figure 4:
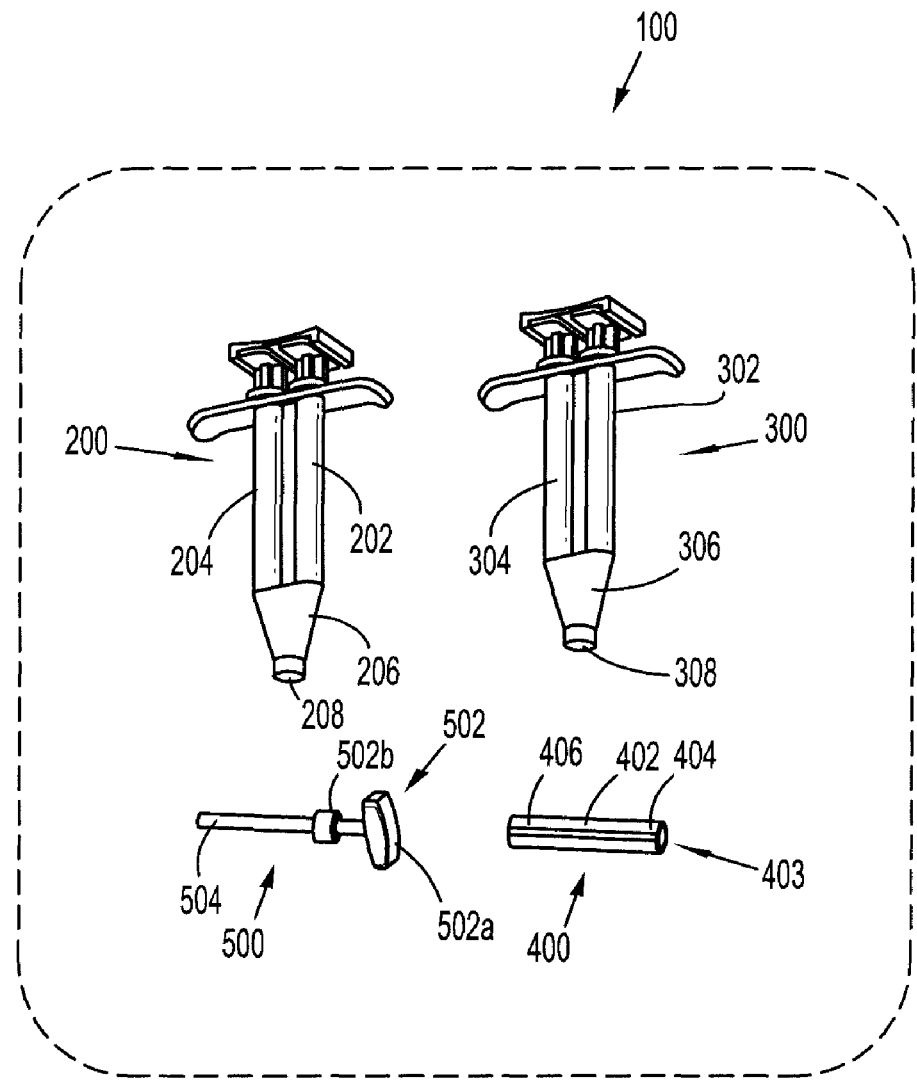
FIG. 4 is a top view of a system for forming a coaxial implant according to an embodiment of the present disclosure.

A system for forming a coaxially layered cylindrical implant will now be described with reference to FIGS. 4-12. Referring initially to FIG. 4, implant forming system 100 includes at least a first dispensing assembly 200, a second dispensing assembly 300, an implant forming sleeve 400, and a centering post 500. Although the system of the present disclosure will be described as relates to a system for forming a coaxially-layered, cylindrical shaped implant 10a (FIG. 12) having a core 20a and a first layer 30a, as will be discussed in further detail below, implant forming system 100 may be modified for use in forming an implant having multiple layers. Additionally, implant forming system 100 may be modified to form an implant having multiple cores 20b (FIG. 13) and/or having different cross-sectional profiles.

With reference still to FIG. 4, first and second dispensing assemblies 200, 300 may include any known assemblies capable of dispensing a material or composition through a distal tip. As shown, first and second dispensing assemblies 200, 300 are substantially similar; however, it is envisioned that first and second dispensing assemblies 200, 300 may be different. Each of first and second dispensing assemblies 200, 300 include respective first and second sources of component 202, 302, 204, 304 and a mixing tip 206, 306, respectively.

Although shown including dispensing assemblies having two sources of component and a mixing tip, it is envisioned that dispensing assemblies having alternative configurations may be used with implant forming system 100. For example, either or both of dispensing assemblies 200, 300 may include only a single source of component and a polymerizing tip that is configured to activate the component as the component passes through the tip. Alternatively, dispensing assemblies 200, 300 may be configured to mix more than two components.

As shown, the first and second sources of components 202, 302, 204, 304 include syringes; however, it is envisioned that other sources of component may be employed. For example, components may be supplied to sleeve 400 using metering pumps, squeeze bags or other dispensing means. It is further envisioned that dispensing assemblies 200, 300 may be configured to mix one or more powdered components with one or more liquid components. Distal ends 208, 308 of mixing tips 206, 306 of respective first and second dispensing assemblies 200, 300 are configured to selectively engage either end 404, 406 of sleeve 400 using any suitable method, including bayonet coupling, friction fit, threads, combinations thereof, and the like.

Still referring to FIG. 4, implant forming sleeve 400 defines an elongated, substantially annular member 402 having first and second ends 404, 406 and defining a longitudinal cavity 403 therebetween. Although shown having a circular cross-section, it is envisioned that sleeve 400 may have a cross-section that is rectangular (FIG. 5A), star-shaped (FIG. 5B), octagonal, (FIG. 5C), hexagonal (FIG. 5D), oval (FIG. 5E), triangular (FIG. 5F), pentagonal (FIG. 5G), diamond (FIG. 5H), trapezoidal (FIG. 5I), cross-shaped (FIG. 5J), or any other suitable configuration, including concave or convex (not shown). Although shown having a substantially cylindrical profile, it is envisioned that sleeve 400 may have alternative profiles including, for example, sleeve 400 may be oblong (FIG. 6A), barbell-shaped (FIG. 6B), stepped (FIG. 6C), curved (FIG. 6 D), or any other suitable configuration. Each of first and second ends 404, 406 is configured for selective engagement with distal ends 208, 308 of respective first and second dispensing assemblies 200, 300. Sleeve 400 may be formed of paper, plastic or polymer. Although, in one embodiment, sleeve 400 is intended to be removed from implant 10 after formation, sleeve 400 may be composed of a degradable material that may remain about implant 10 following implantation. In this manner, sleeve 400 provides an additional layer to implant 10. It is envisioned that the degradable sleeve may be infused with one or more TA and/or API to improve the characteristics of implant 10. In another embodiment, and as shown, sleeve 400 includes one or more zippers 405 (FIG. 10) or perforations formed along a length thereof configured for creating a longitudinal seam 405*a* (FIG. 11) in sleeve 400 such that sleeve 400 may be separated and removed from implant 10. Although not shown, it is envisioned that one or more polymeric layers including one or more TAs and/or APIs may be provided in sleeve 400 prior to forming an implant, such that an implant formed using the sleeve would include one or more extra layers to improve the characteristics of the implant.

In embodiments, an additional layer may include a second sleeve (not shown) within or surrounding sleeve 400. The multiple sleeves may, in embodiments, be formed of the same or different materials forming sleeve 400, including the same or different TAs and/or APIs. In some embodiments, the multiple sleeves may provide a core/shell configuration to the implant.

Each of first and second ends 404, 406 are further configured to selectively engage a base portion 502 of centering post 500. With reference still to FIG. 4, centering post 500 is configured to be received within cavity 403 of sleeve 400 and to selectively engage an end 404, 406 thereof. Centering post 500 includes a base 502 and a post 504 extending from base 502. Base 502 includes a handle portion 502*a* on a proximal end thereof and a plug portion 502*b* on a distal end thereof. Handle portion 502*a* is configured to facilitate engagement of centering post 500 by a clinician. Plug portion 502*b* is configured for selective engagement with an end 404, 406 of sleeve 400. As will be discussed in further detail below, plug portion 502*b* of base 502 effectively seals an end 404, 406 of sleeve 400 to retain components within sleeve 400 until the components have had sufficient time to harden. Post 504 of centering post 500 is configured to create a longitudinal void (not shown) within first layer 30*a* (FIG. 12) of implant 10*a* during formation of first layer 30*a* upon which a second material may be added to form core 20*a*. Post 504 may extend the entire length of sleeve 400 or may only extend partially therethrough. In another embodiment, post 504 may be composed of a biodegradable material and include one or more TAs and/or APIs configured for controlled release. In this manner, post 504 may include a breakaway connection such that post 504 may remain within implant 10 after forming of first layer 30*a* so that post 504 becomes core 20*a*.

Figure 7:
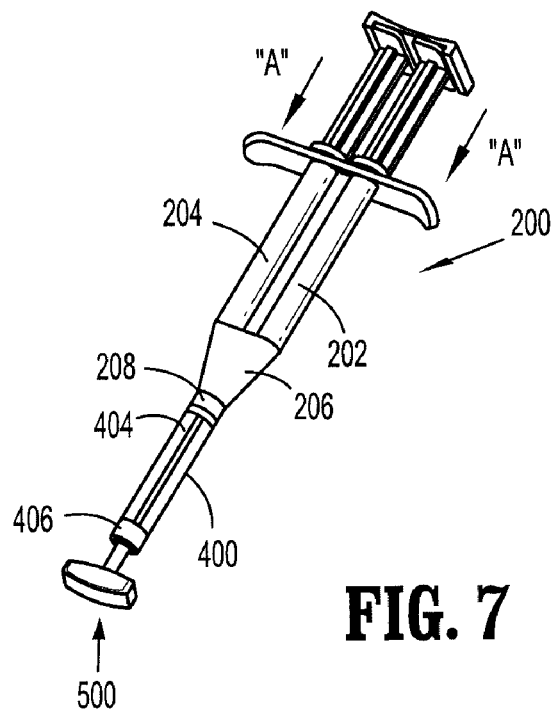
FIG. 7 is a perspective view of the implant forming system of FIG. 4, including a sleeve operably engaged with a first dispensing assembly and a centering post.

The use of implant forming system 100 will now be described with reference to FIGS. 7-14. Referring initially to FIG. 7, first dispensing assembly 200 is selectively connected with first end 404 of implant forming sleeve 400 and centering post 500 is selectively received within second end 406 of sleeve 400. First dispensing assembly 200 may be provided with first and second sources of component 202, 204, respectively, or instead, first and second sources of component may be added to dispensing assembly 200 prior to forming first layer 30*a* of implant 10*a* (FIG. 14). In this manner, the components and resulting first layer 30*a* may be customized for a given procedure. First and second components 202, 204, which form first layer 30*a* of implant 10*a* may include one or more polymeric materials, one or more hydrogels, one or more TAs and/or one or more APIs. Such materials may be activated upon combination or as the resulting mixture passes through mixing tip 206.

Figure 8:
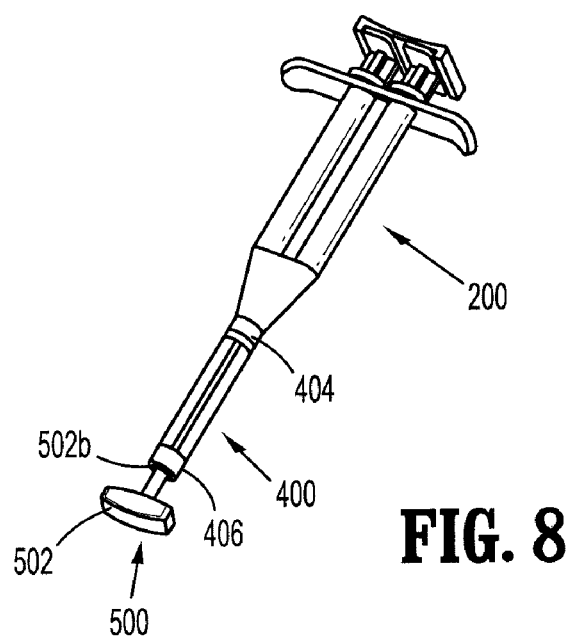
FIG. 8 is a perspective view of the system, including the sleeve, dispensing assembly and post of FIG. 7 following activation of the dispensing assembly.

Turning to FIG. 8, activation of dispensing assembly 200 causes the contents thereof to pass through mixing tip 206 and out distal outlet 208 into cavity 403 of sleeve 400 about post 504 of centering post 500. Activation of dispensing assembly 200 may include powering a mixing assembly, activating a polymerizing light, and/or simply depressing first and second plungers, as indicated by arrows "A" in FIG. 7, to cause the flow of first and second components through mixing tip 208 and into sleeve 400. As discussed above, plug portion 502*b* of base 502 of centering post 500 securely engages end 406 of sleeve 400 thereby sealing end 406 and preventing the material forming first layer 30*a* from leaking from cavity 403 of sleeve 400.

Figure 9:
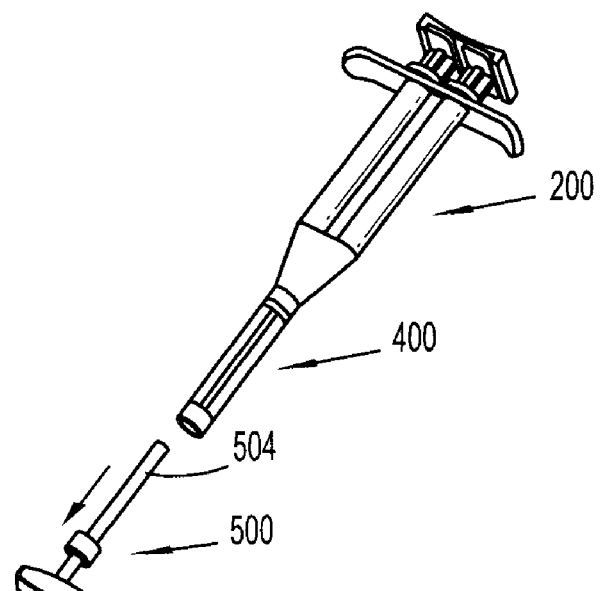
FIG. 9 is a perspective view of a centering plug shown in FIG. 7 removed from the sleeve.

With reference now to FIG. 9, once the material forming first layer 30*a* hardens sufficiently, centering post 500 is separated from second end 406 of sleeve 400 thereby removing post 504 from with cavity 403 thereof. Separation of centering post 500 from sleeve 400 creates a void (not shown) within first layer 30*a* where post 504 once occupied. In an alternative embodiment, centering post 500 may including more than one post 504. As such, the removal of centering post 500 would create more than one void within first layer 30*a*.

Figure 10:
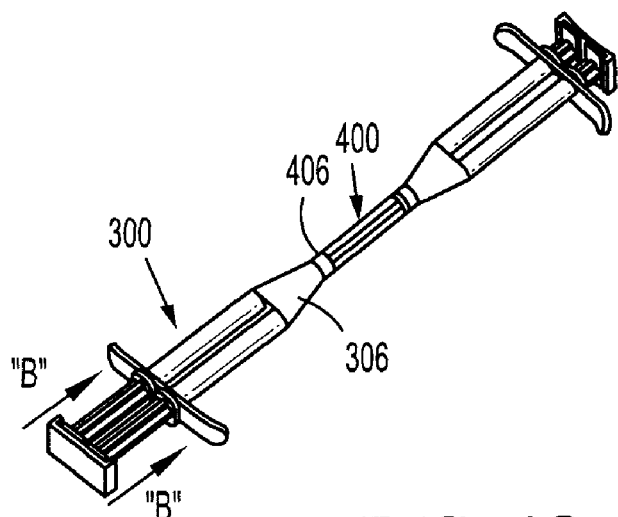
FIG. 10 is a perspective view of a second dispensing assembly engaged with the sleeve.

Turning now to FIG. 10, second dispensing assembly 300 is then selectively attached to second end 406 of sleeve 400. Dispensing assembly 300 is operated in a substantially similar manner to dispensing assembly 200. Activation of dispensing assembly 300, as indicated by arrows "B", causes the contents thereof to pass through mixing tip 306 and into the void (not shown) within sleeve 400 created by the removal of centering post 500. Depending on the length of post 504 of centering post 500, dispensing assembly 200 may seal first end 404 of sleeve 400 while second dispensing assembly 300 seals second end 406 thereof.

Figure 11:
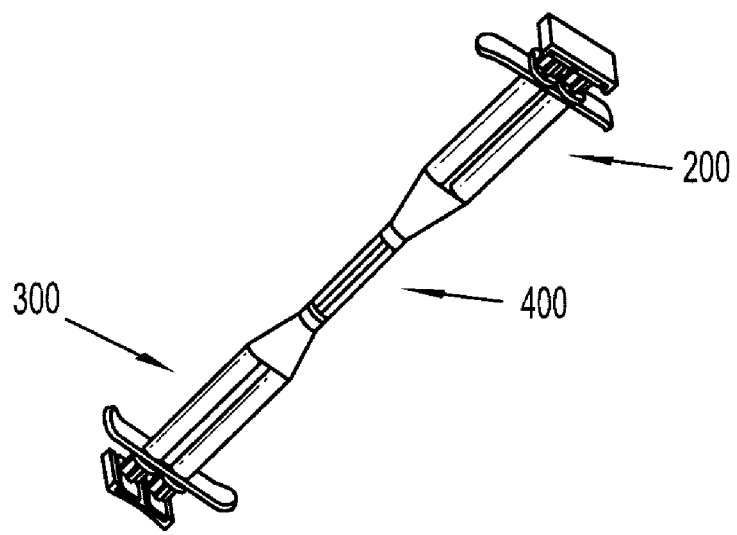
FIG. 11 is a perspective view of the first and second dispensing assemblies and sleeve of FIG. 10 following activation of the second dispensing assembly.

With reference briefly to FIG. 11, once the materials forming core 20*a* have been received with first layer 30*a* of implant 10*a*, first and second dispensing assemblies 200, 300 remain engaged with sleeve 400 until the materials have sufficiently hardened, i.e., such that neither material leaks from sleeve 400 upon disengagement of either first or second dispensing assemblies 200, 300.

Figure 12:
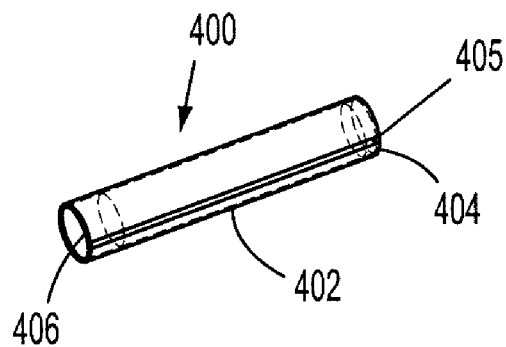
FIG. 12 is a perspective view of the sleeve shown in FIGS. 7-11.

Turning now to FIG. 12, once both core 20*a* and first layer 30*a* have sufficiently hardened, first and second dispensing assemblies 200, 300, are disengaged from sleeve 400. Core 20*a* and first layer 30*a* may require additional time to harden within sleeve 400 before sleeve 400 is removed. As discussed above, in one embodiment, sleeve 400 is configured to remain on implant 10*a*.

Figure 13:
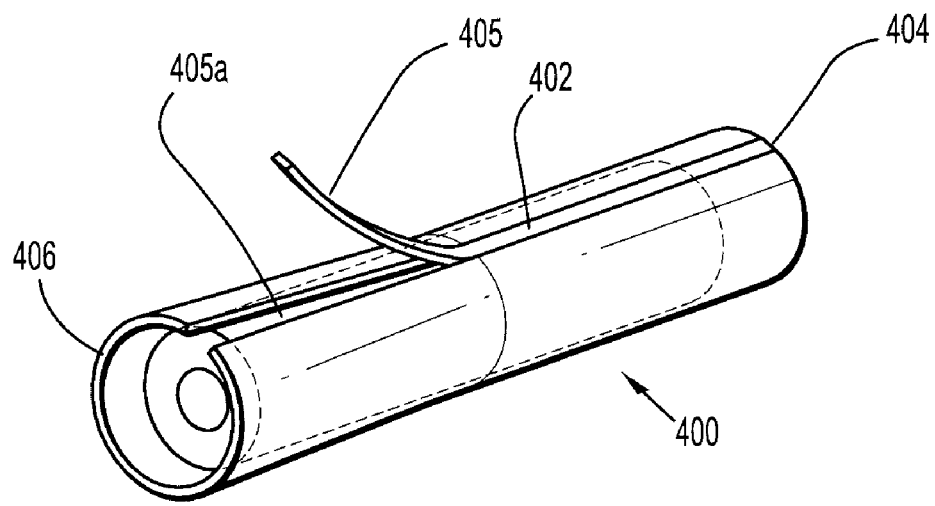
FIG. 13 is a perspective view of the sleeve of FIG. 12 and a coaxial implant formed within the sleeve.
Figure 14:
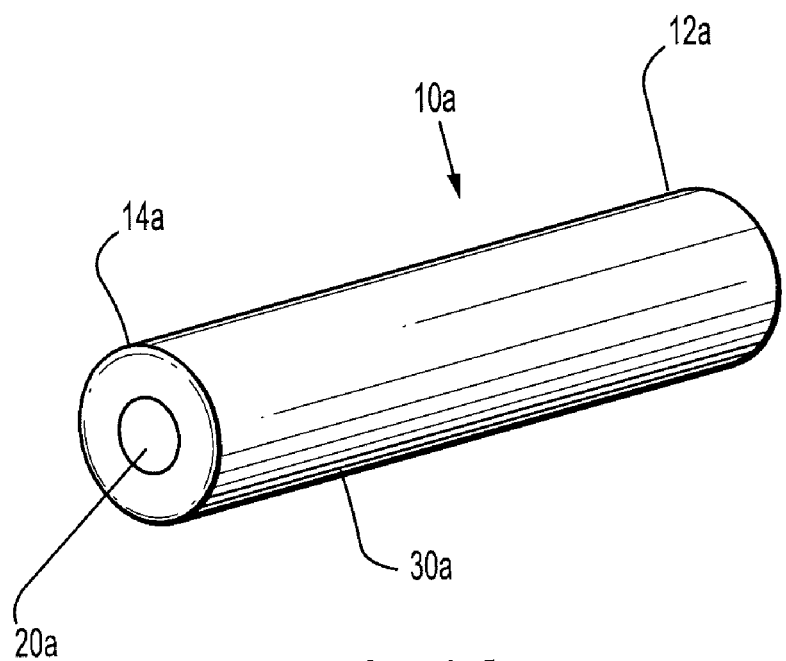
FIG. 14 is a perspective view of the coaxial implant of FIG. 13.

With reference now to FIG. 13, once core 20*a* and first layer 30*a* have sufficiently hardened, sleeve 400 may be separated and removed therefrom. Sleeve 400 is separated from implant 10*a* by pulling on zipper 405 to create seam 405*a* in sleeve 400. Sleeve 400 may then be peeled off of implant 10*a*. As discussed above, in an alternative embodiment, sleeve 400 may be configured to remain on implant 10*a*.

With reference to FIG. 14, implant 10*a* includes core 20*a* extending the entire length thereof and first layer 30*a* coaxially received about core 20a. Implant 10a is then ready for implantation. Alternatively, implant 10a may be further treated. For example, implant 10a may be dipped in a polymeric material to create a protective overcoat. Either or both of first and second ends 12a, 14a of implant 10a may be sealed to prevent premature coaxial release of core 20a.

It is envisioned that implant forming system 100 may further include one or more additional sleeves (not shown) and/or one or more additional dispensing assemblies (not shown). Each additional sleeve and/or dispensing assembly may be used to provide implant 10a with an additional layer of material.

Figure 15:
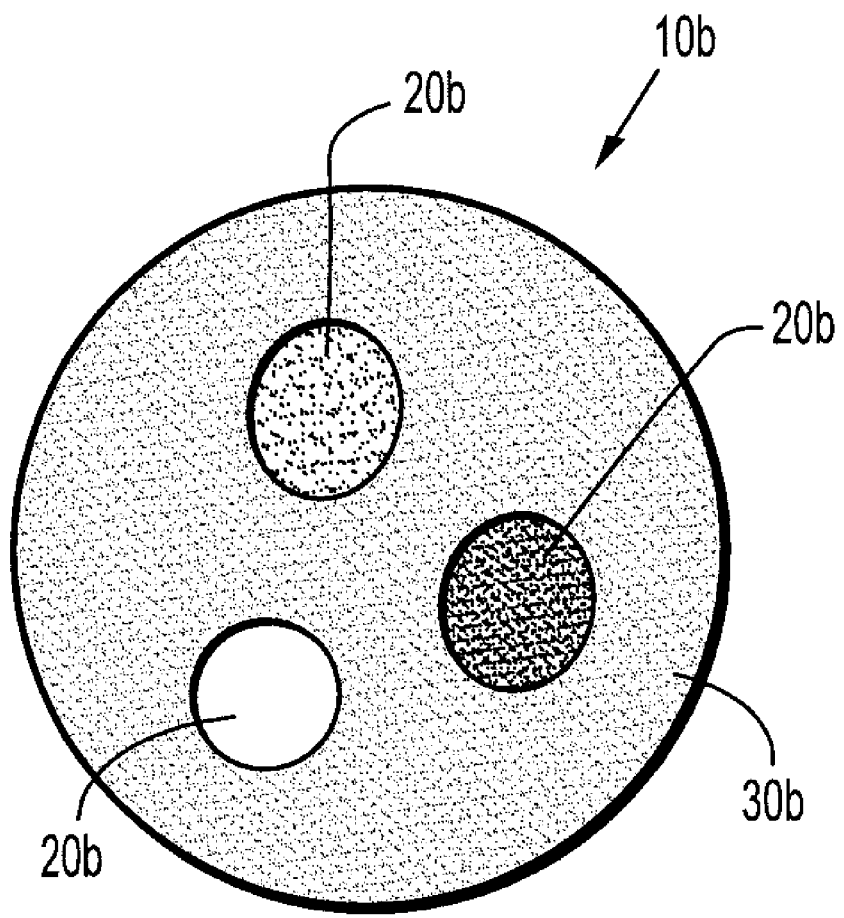
FIG. 15 is cross-section end view of another embodiment of an implant according to the present disclosure.

With reference to FIG. 15, an implant constructed in accordance with an alternative embodiment of a system for forming an implant is shown generally as implant 10b. Implant 10b includes multiple cores 20b. Cores 20b may be formed of the same or different materials. It is envisioned that multiple core implant 10b may be formed using a modified centering post having multiple posts. Each of the posts forming the modified centering post may be removed individually to create individual voids. Initially, layer 30b is formed about each of the posts as described above, by activating a first dispensing assembly. Once first layer 30b has sufficiently hardened, a first of the posts is removed to create a first void within first layer 30b. The first dispensing assembly may then be removed from a first end of the sleeve and replaced by a second dispensing assembly. The second dispensing assembly may then be activated to deposit a material with the first void. Once this material has sufficient hardened, a second of the posts is removed from the sleeve to create a second void in the first layer. The second dispensing assembly may then be removed from the first end of the sleeve and be replaced by a third dispensing assembly for depositing another material within the second void. This process may be repeated to create an implant having any number of cores 20b.

As noted above, the implant of the present disclosure may be utilized to deliver one or more therapeutic agents (TAs) and/or one or more active pharmaceutical ingredients (APIs) which may, in embodiments, be collectively referred to herein as "bioactive agents." The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent, which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present implant in any suitable form of matter, e.g., films, powders, liquids, gels and the like.

Examples of classes of bioactive agents, which may be utilized in accordance with the present disclosure for example, include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; anti-spasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the implant and the surrounding tissues to which the implant is applied. In addition, anti-adhesive agents may be used to prevent adhesions from forming between the formed implant and the sleeve described above. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents, which may be included as a bioactive agent include: triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides, such as tobramycin and gentamicin, rifampicin, bacitracin, neomycin, chloramphenicol, and miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins; cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be delivered by an implant of the present disclosure include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

The implant of the present disclosure may also include, for example, biologically acceptable plasticizers, antioxidants, and/or colorants, which can be impregnated into the medical device.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, a first longitudinal section of the core and/or any or all of the layers may be formed of a different composition than one or more subsequent longitudinal sections of the core and/or any or all of the layers.

What is claimed is:

1. A system for forming a coaxial implant, the system comprising:
   a first assembly for dispensing a first material;
   a second assembly for dispensing a second material;
   a sleeve defining first and second ends and defining a cavity therebetween for forming an implant, wherein the first and second ends are configured for operable engagement with each of the first and second assemblies; and
   a centering post configured for operable engagement with the sleeve.

2. The system of claim 1, wherein at least one of the first and second materials include at least one of a therapeutic agent and an active pharmaceutical ingredient.

3. The system of claim 1, wherein each of the first and second materials comprises a hydrogel.

4. The system of claim 1, wherein at least one of the first and second assemblies includes a mixing tip.

5. The system of claim 1, wherein both the first and second assemblies include a mixing tip.

6. The system of claim 1, wherein the first assembly is configured to mix at least a first and second component.

7. The system of claim 1, wherein the sleeve includes a zipper for creating a seam in the sleeve.

8. The system of claim 7, wherein the seam enables removal of the sleeve from about an implant formed therein.

9. The system of claim 1, wherein the sleeve includes a non-circular cross-sectional profile.

10. A method of forming a coaxial implant, the method comprising the steps of:
    providing a system including first and second dispensing assemblies, an implant forming sleeve having two ends, and a centering post;
    selectively securing the first dispensing assembly with a first end of the implant forming sleeve and the centering post with a second end of the implant forming sleeve;
    activating the first dispensing assembly to deposit a first material within the sleeve and about the centering post to form a first layer of the implant;
    separating the centering post from the second end of the sleeve thereby creating a void with the first layer;
    selectively securing the second dispensing assembly with the second end of the implant forming sleeve;
    activating the second dispensing assembly to deposit a second material within the void to form a core of the implant; and
    separating the first and second dispensing assemblies from the sleeve.

11. The method of claim 10 further including the step of removing the sleeve from about the implant.

12. The method of claim 10, wherein at least one of the first and second materials include at least one of a therapeutic agent and an active pharmaceutical ingredient.

13. The method of claim 10, wherein each of the first and second materials includes at least one of a therapeutic agent and an active pharmaceutical ingredient.

14. The method of claim 13, wherein the therapeutic agent and active pharmaceutical ingredient in the first material and the second material are the same or different.

15. The method of claim 10, wherein at least one of the first and second materials comprises a hydrogel.

16. The method of claim 15, wherein at least one of the first and second materials comprises a biocompatible polymer.

17. The method of claim 10, wherein each of the first and second materials comprises a hydrogel.

* * * * *